US012780812B2

(12) United States Patent
Karjalainen

(10) Patent No.: US 12,780,812 B2
(45) Date of Patent: Nov. 3, 2026

(54) PROCESS FOR THE PREPARATION OF A CYP11A1 INHIBITOR AND INTERMEDIATES THEREOF

(71) Applicant: Orion Corporation, Espoo (FI)

(72) Inventor: Oskari Karjalainen, Espoo (FI)

(73) Assignee: ORION CORPORATION, Espoo (FI)

( * ) Notice: Subject to any disclaimer, the term of this patent is extended or adjusted under 35 U.S.C. 154(b) by 473 days.

(21) Appl. No.: 18/548,486

(22) PCT Filed: Feb. 28, 2022

(86) PCT No.: PCT/FI2022/050127
§ 371 (c)(1),
(2) Date: Aug. 30, 2023

(87) PCT Pub. No.: WO2022/184975
PCT Pub. Date: Sep. 9, 2022

(65) Prior Publication Data

US 2024/0174654 A1 May 30, 2024

(30) Foreign Application Priority Data

Mar. 1, 2021 (FI) ..................................... 20215216

(51) Int. Cl.
*C07D 405/14* (2006.01)
*C07D 211/96* (2006.01)
*C07D 309/32* (2006.01)
*C07D 405/06* (2006.01)

(52) U.S. Cl.
CPC .......... *C07D 405/14* (2013.01); *C07D 211/96* (2013.01); *C07D 309/32* (2013.01); *C07D 405/06* (2013.01)

(58) Field of Classification Search
CPC ................ C07D 405/14; C07D 211/96; C07D 309/32; C07D 405/06
See application file for complete search history.

(56) References Cited

U.S. PATENT DOCUMENTS

| | | | |
|---|---|---|---|
| 6,426,418 | B1 | 7/2002 | Tam et al. |
| 10,717,726 | B2 | 7/2020 | Belle et al. |
| 11,098,032 | B2 | 8/2021 | Belle et al. |
| 2014/0275043 | A1 | 9/2014 | Kuksa et al. |
| 2019/0359601 | A1 | 11/2019 | Belle et al. |
| 2020/0299280 | A1 | 9/2020 | Belle et al. |
| 2021/0347765 | A1 | 11/2021 | Belle et al. |
| 2023/0192677 | A1 | 6/2023 | Belle et al. |

FOREIGN PATENT DOCUMENTS

| | | | |
|---|---|---|---|
| JP | 2005-536501 | A | 12/2005 |
| WO | WO 2004006925 | A | 1/2004 |
| WO | WO 2009085185 | A1 | 7/2009 |
| WO | WO 2018115591 | A1 | 6/2018 |
| WO | WO 2020264499 | A1 | 12/2020 |
| WO | WO 2022184977 | A1 | 9/2022 |
| WO | WO 2022184978 | A1 | 9/2022 |
| WO | WO 2023139312 | A1 | 7/2023 |

OTHER PUBLICATIONS

International Search Report and Written Opinion mailed May 6, 2022 for International PCT Application No. PCT/FI2022/050127 (18 pages).
Tilstam et al., 2012, "Sulfolane: A Versatile Dipolar Aprotic Solvent", Organic Process Research & Development 16(7):1273-1278.

*Primary Examiner* — Renee Claytor
*Assistant Examiner* — Christopher Lindsay Johnson
(74) *Attorney, Agent, or Firm* — Jones Day

(57) ABSTRACT

The present invention relates to an improved process for the preparation of 4H-pyranone structured CYP11A1 inhibitors such as 2-(isoindolin-2-ylmethyl)-5-((1-(methylsulfonyl)piperidin-4-yl)methoxy)-4H-pyran-4-one (1A) and key intermediates thereof such as 2-(chloromethyl)-5-hydroxy-4H-pyran-4-one (II), 5-hydroxy-2-(isoindolin-2-ylmethyl)-4H-pyran-4-one (III), (1-(methylsulfonyl)piperidin-4-yl)methyl methane sulfonate (V') and (1-(methyl-sulfonyl)piperidin-4-yl)methyl 4-methylbenzene sulfonate (V"). CYP11A1 inhibitors are useful in the treatment of hormonally regulated cancers, such as prostate cancer and breast cancer.

20 Claims, No Drawings

PROCESS FOR THE PREPARATION OF A CYP11A1 INHIBITOR AND INTERMEDIATES THEREOF

RELATED APPLICATIONS

This application is a U.S. National Stage filing under 35 U.S.C. § 371 of International Application No. PCT/FI2022/050127, filed Feb. 28, 2022, which claims the benefit of Finish application No. 20215216, filed Mar. 1, 2021, the disclosure of each of which is incorporated herein by reference in its entirety.

TECHNICAL FIELD

The present invention relates to an improved process for the preparation of 4H-pyranone structured CYP11A1 inhibitors such as 2-(isoindolin-2-ylmethyl)-5-((1-(methylsulfonyl)piperidin-4-yl)methoxy)-4H-pyran-4-one (1A) and key intermediates thereof such as 2-(chloromethyl)-5-hydroxy-4H-pyran-4-one (II), 5-hydroxy-2-(isoindolin-2-ylmethyl)-4H-pyran-4-one (III), (1-(methylsulfonyl)piperidin-4-yl) methyl methane sulfonate (V') and (1-(methyl-sulfonyl) piperidin-4-yl)methyl 4-methylbenzene sulfonate (V").

BACKGROUND OF THE INVENTION

The compound 2-(isoindolin-2-ylmethyl)-5-((1-(methylsulfonyl)piperidin-4-yl)methoxy)-4H-pyran-4-one of formula (1A) and derivatives thereof have been disclosed in WO 2018/115591. Compound of formula (1A) is a selective inhibitor of CYP11A1 enzyme and is useful in the treatment of hormonally regulated cancers, such as prostate cancer and breast cancer.

(1A)

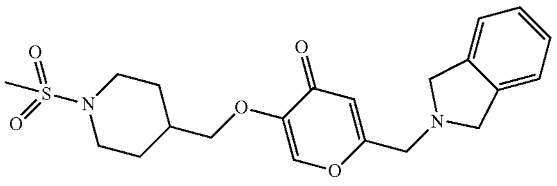

WO 2018/115591 discloses a process for the preparation of the compound of formula (1A) according to Scheme 1.

SCHEME 1.

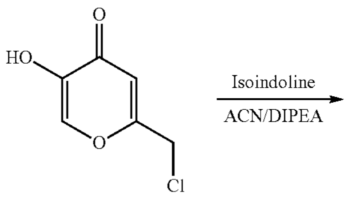

(II)

-continued

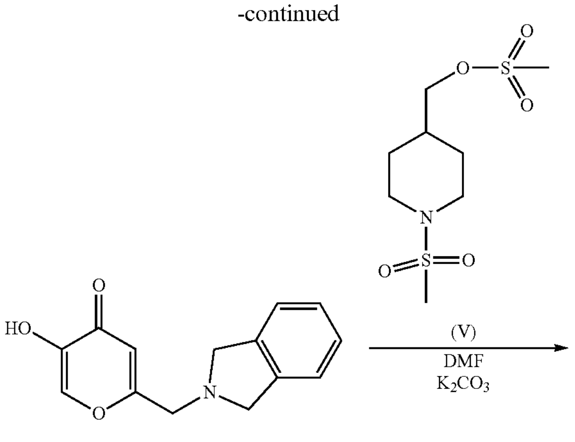

(III)

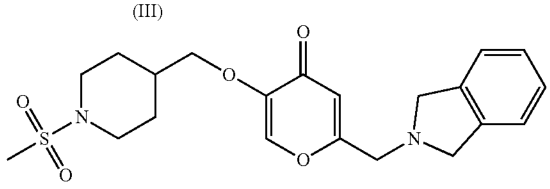

(1A)

This process comprises reacting 2-(chloromethyl)-5-hydroxy-4H-pyran-4-one (II) with isoindoline in acetonitrile in the presence of N,N-diisopropylethylamine (DIPEA) to obtain 5-hydroxy-2-(isoindolin-2-ylmethyl)-4H-pyran-4-one (III) followed by reaction with (1-(methylsulfonyl) piperidin-4-yl)methyl methane sulfonate (V) in dimethylformamide (DMF) in the presence of potassium carbonate base. The compound of formula (1A) is recovered from the reaction mixture by addition of water, extracting with EtOAc and evaporating to dryness followed by purification by column chromatography.

The above mentioned process has several drawbacks. The yield of the first step for obtaining compound of formula (III) is poor, not higher than about 36%, and large volumes of solvent is needed. The final step suffers from the need to evaporate the solvent to dryness for obtaining the brownish crude product, which needs to be purified by column chromatography leading to poor yield. The process does not provide the possibility of crystallization the end product directly from the solvent.

Thus, there is a need for a more practical and economical process that is suitable for the manufacture of compound (1A) and intermediates thereof in the large scale.

SUMMARY OF THE INVENTION

It has now been found that the compound of formula (1A) and its intermediates can be prepared using a process, which is more practical, economical and suitable for use in a large scale. In particular, the compound of formula (1A) and intermediates thereof can be obtained in significantly higher yields and with lower solvent volumes. Moreover, the compound of formula (1A) is obtained as a high purity and low colored product directly by crystallization without the need of purification by chromatography.

Thus, the present invention provides a process for the preparation of a compound of formula (1A) or a pharmaceutically acceptable salt thereof (1A)

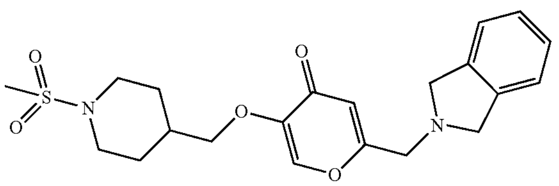

comprising the steps of either a) reacting a compound of formula (III)

(III)

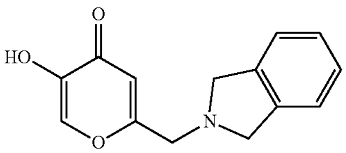

with a compound of formula (V), (V)

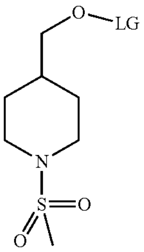

wherein LG is a leaving group selected from a mesyl or a tosyl group, in sulfolane in the presence of cesium carbonate;

b) adding acetone and water to the mixture; and c) isolating the compound of formula (1A), and optionally converting it to its pharmaceutically acceptable salt;

or a') reacting a compound of formula (III)

(III)

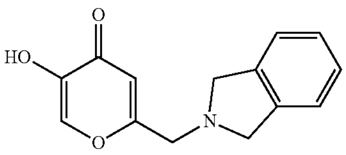

with a compound of formula (V), (V)

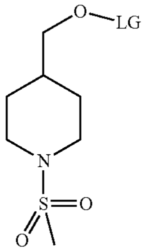

wherein LG is a leaving group selected from a mesyl or a tosyl group, in dimethyl sulfoxide or dimethyl formamide at an elevated temperature in the presence of cesium carbonate and tris[2-(2-methoxyethoxy)ethyl]amine);

b') adding isopropanol and water to the mixture; and c') isolating the compound of formula (1A), and optionally converting it to its pharmaceutically acceptable salt.

In another aspect, the present invention provides a process for the preparation of a compound of formula (III)

(III)

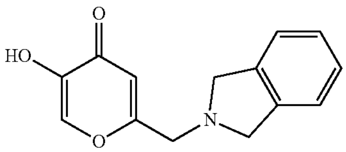

comprising the steps of either a) reacting a compound of formula (II)

(II)

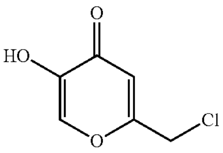

with isoindoline hydrochloride in water in the presence of potassium hydroxide;

b) transferring the reaction mixture of step a) into a mixture of acetone and acetic acid; and c) isolating the compound of formula (III);

or a') reacting a compound of formula (II)

(II)

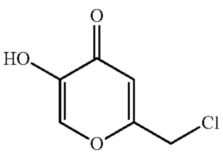

with isoindoline hydrochloride in dimethyl sulfoxide in the presence of N,N-diisopropylethylamine;

b') adding acetonitrile and water to the mixture; and c') isolating the compound of formula (III).

In still another aspect, the present invention provides a process for the preparation of a compound of formula (V')

(V')

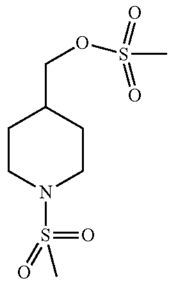

comprising the steps of a) reacting a compound of formula (IV)

(IV)

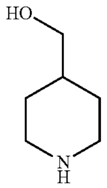

with methanesulfonyl chloride in acetonitrile-pyridine solvent;

b) adding water and acetic acid to the mixture; and c) isolating the compound of formula (V).

In still another aspect, the present invention provides a process for the preparation of a compound of formula (V")

(V")

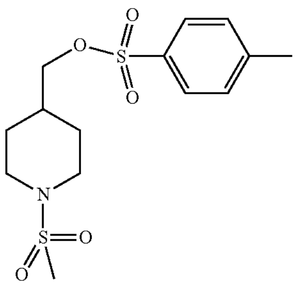

comprising the steps of a) reacting a compound of formula (IV)

(IV)

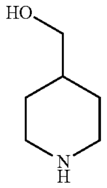

with chlorotrimethylsilane to obtain compound of formula (IVb)

(IVb)

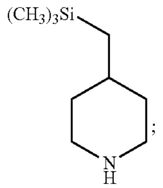

b) reacting the compound of formula (IVb) with methanesulfonyl chloride to obtain a compound of formula (IVc)

(IVc)

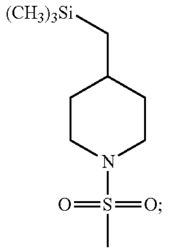

c) treating the compound of formula (IVc) with p-toluenesulfonic acid in the presence of methanol to obtain a compound of formula (IVd)

(IVd)

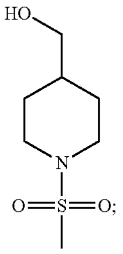

and d) reacting the compound of formula (IVd) with p-toluenesulfonyl chloride to obtain the compound of formula (V").

In still another aspect, the present invention provides a process for the preparation of a compound of formula (1A) or a pharmaceutically acceptable salt thereof (1A)

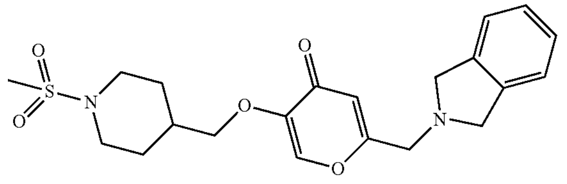

comprising the steps of either a) reacting a compound of formula (II)

(II)

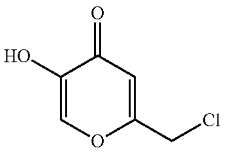

with isoindoline hydrochloride in water in the presence of potassium hydroxide;

b) transferring the reaction mixture of step a) into a mixture of acetone and acetic acid; and c) isolating the compound of formula (III);

or a') reacting a compound of formula (II)

(II)

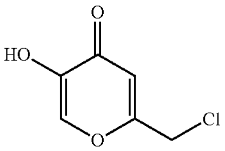

with isoindoline hydrochloride in dimethyl sulfoxide in the presence of N,N-diisopropylethylamine;

b') adding acetonitrile and water to the mixture; and c') isolating the compound of formula (III);

d) either reacting a compound of formula (III)

(III)

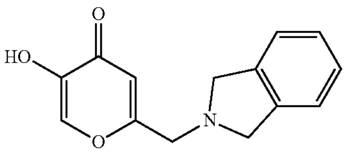

with a compound of formula (V)

(V)

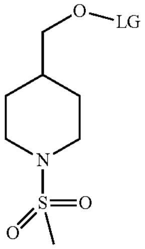

wherein LG is a leaving group selected from a mesyl or a tosyl group, in sulfolane in the presence of cesium carbonate;

e) adding acetone and water to the mixture; and f) isolating the compound of formula (1A), which is optionally converted to its pharmaceutically acceptable salt;

or d') reacting a compound of formula (III)

(III)

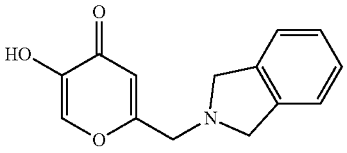

with a compound of formula (V)

(V)

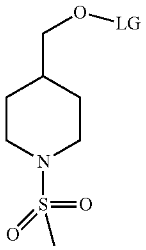

wherein LG is a leaving group selected from a mesyl or a tosyl group, in dimethyl sulfoxide or dimethyl formamide at an elevated temperature in the presence of cesium carbonate and tris[2-(2-methoxyethoxy)ethyl]amine);

e') adding isopropanol and water to the mixture; and f') isolating the compound of formula (1A), which is optionally converted to its pharmaceutically acceptable salt.

DETAILED DESCRIPTION OF THE INVENTION

According to one embodiment of the invention, 2-(isoindolin-2-ylmethyl)-5-((1-(methylsulfonyl)piperidin-4-yl)methoxy)-4H-pyran-4-one of formula (1A) or a pharmaceutically acceptable salt thereof can be prepared using the method comprising the steps of a) reacting 5-hydroxy-2-(isoindolin-2-ylmethyl)-4H-pyran-4-one of formula (III)

(III)

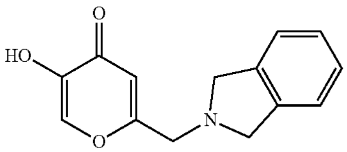

with (1-(methylsulfonyl)piperidin-4-yl)methyl methane sulfonate of formula (V)

(V)

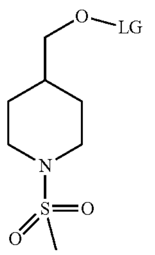

wherein LG is a leaving group selected from a mesyl or a tosyl group, in sulfolane in the presence of cesium carbonate;

b) adding acetone and water to the mixture; and c) isolating the compound of formula (1A), and optionally converting it to its pharmaceutically acceptable salt.

According to one embodiment of this method, the compound of formula (V) is (1-(methylsulfonyl)piperidin-4-yl) methyl methane sulfonate (V').

(V')

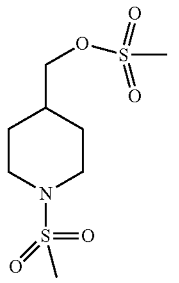

According to another embodiment of this method, the compound of formula (V) is (1-(methylsulfonyl)piperidin-4-yl)methyl 4-methylbenzene sulfonate (V"):

(V")

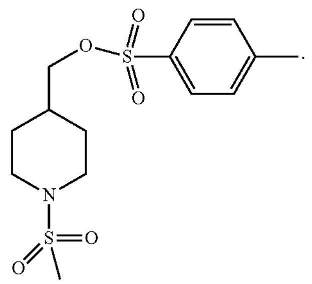

For carrying out the method, sulfolane solvent, 5-hydroxy-2-(isoindolin-2-ylmethyl)-4H-pyran-4-one (III), (1-(methylsulfonyl)piperidin-4-yl)methyl methane sulfonate (V') or (1-(methylsulfonyl)piperidin-4-yl)methyl 4-methylbenzenesulfonate (V") and cesium carbonate are added to the reaction vessel which is preferably under nitrogen atmosphere. The amount of sulfolane is suitably about 500 ml per 100 g of the starting compound (III). The reaction can be conducted at an elevated temperature ranging typically from about 70° C. to about 90° C., for example at 80±5° C. The mixture is stirred at this temperature for a time period sufficient to complete the reaction. The reaction time is generally about 1-6 h, typically about 2-4 h. After completion of the reaction, the mixture is suitably cooled to a temperature ranging from about 45° C. to about 60° C., for example to about 55° C. Thereafter acetone is added to the mixture followed by water while keeping the temperature of the resulting mixture over 45° C., for example within the range of 50-55° C. The ratio of acetone to water is suitably from about 1:1 to about 1:3, for example about 1:2, per volume. The ratio of acetone/water mixture to sulfolane is suitably about 1.5:1 per volume. If desired, the mixture may be seeded at this stage followed by stirring, typically for about 0.5-1 h. Thereafter, the mixture is slowly cooled to a temperature which may range typically form about 5° C. to about 25° C., for example to 15±5° C. The cooling is suitably carried out during about 1 h to 6 h, for example during about 3 h. The mixture is then stirred for a period sufficient to complete precipitation, typically about 2 h, prior to isolation of the end product, for example by filtering. The product can be washed with water and isopropanol and dried, for example, under reduced pressure at about 40-60° C. to afford the compound of formula (1A). The method produces low colored, high purity compound of formula (1A) as prismatic, bulky crystals with good processability and filterability.

Alternatively 2-(isoindolin-2-ylmethyl)-5-((1-(methylsulfonyl)piperidin-4-yl)methoxy)-4H-pyran-4-one of formula (1A) or a pharmaceutically acceptable salt thereof can be prepared using the method comprising the steps of a') reacting a compound of formula (III)

(III)

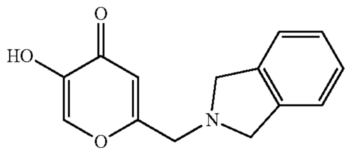

with a compound of formula (V)

(V)

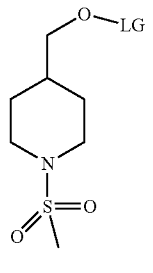

wherein LG is a leaving group selected from a mesyl or a tosyl group, in dimethyl sulfoxide or dimethyl formamide at an elevated temperature in the presence of cesium carbonate and tris[2-(2-methoxyethoxy)ethyl]amine);

b') adding isopropanol and water to the mixture; and c') isolating the compound of formula (1A), and optionally converting it to its pharmaceutically acceptable salt.

According to one embodiment of this method, the compound of formula (V) is (1-(methylsulfonyl)piperidin-4-yl) methyl methane sulfonate (V').

(V')

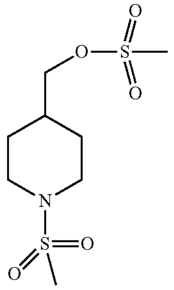

According to another embodiment of this method, the compound of formula (V) is (1-(methylsulfonyl)piperidin-4-yl)methyl 4-methylbenzenesulfonate (V"):

(V")

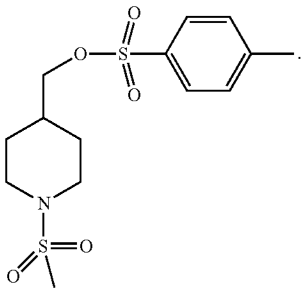

The method can be carried out by adding dimethyl sulfoxide or dimethyl formamide solvent, 5-hydroxy-2-(isoindolin-2-ylmethyl)-4H-pyran-4-one (III), (1-(methyl-sulfonyl)piperidin-4-yl)methyl methane sulfonate (V') or (1-(methyl-sulfonyl)piperidin-4-yl)methyl 4-methylbenzenesulfonate (V") and tris[2-(2-methoxyethoxy)ethyl]amine) (TDA-1)#o the reaction vessel which is preferably under nitrogen atmosphere. The amount of dimethyl sulfoxide or dimethyl formamide is suitably about 500 ml per 100 g of the starting compound (III). The reaction can be conducted at an elevated temperature. If dimethyl sulfoxide is used, the reaction temperature is suitably from about 50° C. to about 70° C., for example about 60° C. If dimethyl formamide is used, the reaction temperature is suitably from about 65° C. to about 75° C., for example about 70° C. The mixture is stirred at this temperature for a time period sufficient to complete the reaction. The reaction time ranges generally from about 1 h to about 8 h, typically from about 2 h to about 5 h. After completion of the reaction, isopropanol is added to the mixture followed by water while keeping the temperature of the resulting mixture over about 50° C. The ratio of isopropanol to water is suitably from about 1:1 to about 1:3, for example about 1:2, per volume. The ratio of isopropanol/water mixture to dimethyl sulfoxide or dimethyl formamide is suitably in the range of from about 1.5:1 to about 2:1, per volume. If desired, the mixture may be seeded at this stage followed by stirring, typically for about 0.5 h-1 h. Thereafter, the mixture is slowly cooled to a temperature which may range typically form about 5° C. to about 25° C., for example to 15±5° C. The cooling is suitably carried out during about 1 h to 6 h, for example during about 3 h. The mixture is then stirred for a period sufficient to complete precipitation, for example about 2 h, prior to isolation of the end product, for example by filtering. The product can be washed with water and isopropanol and dried, for example, under reduced pressure at about 40-60° C. to afford the compound of formula (1A).

If desired, compound (1A) may be converted to a pharmaceutically acceptable salt thereof by methods known in the art.

Compound of Formula (III)

(III)

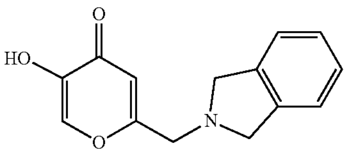

can be prepared by a method comprising the steps of a) reacting a compound of formula (II)

(II)

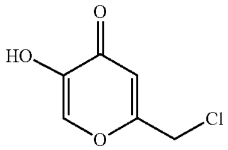

with isoindoline hydrochloride in water in the presence of potassium hydroxide;

b) transferring the reaction mixture of step a) into a mixture of acetone and acetic acid; and c) isolating the compound of formula (III).

It was unexpectedly found that the above reaction for producing the compound of formula (III) can be carried out in water without the use of organic bases. For carrying out this method, water and isoindoline hydrochloride are added to the reaction vessel which is preferably under nitrogen atmosphere. The temperature of this mixture is preferably adjusted to about 5±5° C. Aqueous potassium hydroxide, for example KOH (48%), is then added followed by 2-(chloromethyl)-5-hydroxy-4H-pyran-4-one of formula (II). Thereafter more aqueous potassium hydroxide can be added slowly while keeping temperature at about 10±5° C. The amount of water is suitably about 500 ml per 100 g of the starting compound (II). The mixture is held at the temperature which is from about 0 to about 20° C., for example about 10±5° C., for a time period sufficient to complete the reaction. The reaction time ranges generally from about 1 h to about 6 h, typically from about 2 h to about 4 h. For isolating compound (III) by crystallization a second vessel is charged with a mixture of acetone and acetic acid and heated to about 35±5° C. The ratio of acetone to acetic acid is suitably from about 10:1 to about 6:1, for example about 8:1, per volume. The content of the first vessel is then transferred slowly, for example within about 0.5-1 h, to the second vessel while keeping the temperature in the range from about 30° C. to about 40° C. The ratio of acetone/acetic acid mixture to water after the transfer is suitably in the range of from about 2:1 to about 1:2, for example about 1:1, per volume. The mixture is stirred for a period sufficient to complete precipitation, for example for about 0.5 h-2 h, prior to isolation of the end product, for example by filtering. The product can be washed with water and acetone and dried, for example, under reduced pressure at about 40-60° C. The method produces low colored, high purity compound of formula (III). Transfer of the reaction mixture into the crystallization vehicle produces the end product in crystalline form characterized by good processability and filterability. In contrast, adding the crystallization vehicle into the reaction mixture produces compound of formula (III) in a form which is mud-like and poorly filterable.

Alternatively, 5-hydroxy-2-(isoindolin-2-ylmethyl)-4H-pyran-4-one of formula (III) can be prepared using the method comprising the steps of a') reacting a compound of formula (II)

(II)

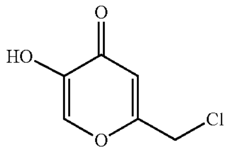

with isoindoline hydrochloride in dimethyl sulfoxide in the presence of N,N-diisopropylethylamine;

b') adding acetonitrile and water to the mixture; and c') isolating the compound of formula (III).

This method can be carried out by adding dimethyl sulfoxide, isoindoline hydrochloride and 2-(chloromethyl)-5-hydroxy-4H-pyran-4-one (II) to the reaction vessel under nitrogen. The amount of dimethyl sulfoxide is suitably about 500 ml per 100 g of the starting compound (II). N,N-diisopropylethylamine (DIPEA) is then added to the reaction mixture. The amount of DIPEA is suitably about 250 ml per 100 g of the starting compound (II). The mixture is then stirred at a temperature which is typically from about 40° C. to about 60° C., for example 50±5° C., for a time period sufficient to complete the reaction. The reaction time ranges generally from about 1 h to about 6 h, and is typically about 2 h-3 h. Thereafter, acetonitrile and optionally acetic acid are added to the reaction mixture. The temperature is suitably adjusted to about 40-60° C., for example 45±5° C. Water is then added slowly under stirring, for example within 0.5 h-1 h, while keeping the temperature over 45° C. The ratio of acetonitrile to water is suitably from about 1:1 to about 1:3, for example about 1:2, per volume. The mixture may be stirred for about 0.5 h and then cooled to a temperature which is from about 10° C. to about 30° C., for example 20±5° C. The cooling is suitably carried out during about 0.5 h-3 h, for example during about 1 h. The mixture is stirred for a period sufficient to complete the precipitation. The precipitated mass can be isolated, for example by filtering, washed with water and acetonitrile and dried, for example, under reduced pressure at about 40-60° C. to afford crystalline compound of formula (III).

Compound of Formula (II)

(II)

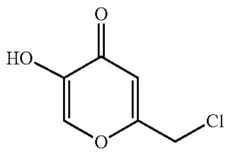

can suitably be prepared by reacting a compound of formula (I)

(I)

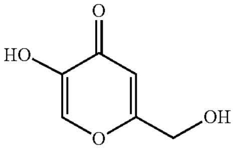

with thionyl chloride in acetonitrile, adding water, cooling the mixture and isolating the compound of formula (II).

For carrying out this method acetonitrile and kojic acid (I) are added to the reaction vessel under nitrogen. The amount of acetonitrile is suitably about 350 ml per 100 g of the starting compound (I). The mixture is suitably heated to a temperature which is from about 30° C. to about 60° C., for example 45±5° C. Thionyl chloride is then added slowly, for example during about 0.5 h-1 h, while keeping temperature at about 45±5° C. The mixture is stirred for a time period sufficient to complete the reaction, for example about 0.5 h-1 h. Water is then added slowly, for example over about 0.5 h-1 h, while keeping temperature at about 45±5° C. The ratio of water to acetonitrile is suitably from about 1:1.5 to about 1:2, for example about 1:1.75. The mixture is stirred at this temperature for least 0.5 h before cooling, for example to a temperature which is from about 0° C. to about 10° C. The cooling is carried out slowly, for example during about 2 h-8 h. The precipitated mass can then be isolated, for example by filtering, washed with water and acetonitrile and dried, for example under reduced pressure at about 40-60° C., to afford crystalline compound of formula (II).

Compound of Formula (V')

(V')

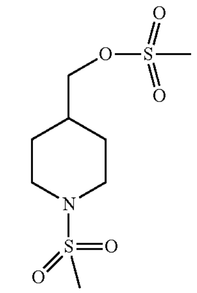

can be prepared using the method comprising the steps of a) reacting a compound of formula (IV)

(IV)

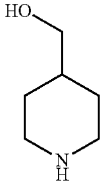

with methanesulfonyl chloride in acetonitrile-pyridine solvent;

b) adding water and acetic acid to the mixture; and c) isolating the compound of formula (V').

The method can be carried out by adding to a reactor vessel under nitrogen acetonitrile, pyridine and piperidin-4-ylmethanol (IV). The ratio of acetonitrile to pyridine at step is typically from about 1:2 to about 2:1, for example about 1:1, per volume. The amount of acetonitrile/pyridine mixture is suitably from about 600 ml to about 700 ml per 100 g of the starting compound (IV). Methanesulfonyl chloride is added slowly, for example during 0.5 h-1 h, while keeping temperature below 35° C. The temperature of the mixture may then be adjusted to about 25-50° C., for example to 35±5° C., and stirred for a time period sufficient to complete the reaction. The reaction time is generally from about 1 h to about 6 h, typically about 2 h-3 h. Thereafter water is rapidly added to the mixture followed by acetic acid. The ratio of water to acetic acid may be from about 5:1 to about 10:1, for example about 7:1, per volume. The mixture is then cooled to a temperature which is from about −10° C. to about 10° C., for example 0±5° C. The cooling may be carried out during about 1 h-6 h, for example during about 3 h followed by stirring for a period sufficient to complete precipitation, for example about 1 h, prior to isolation of the end product, for example by filtering. The precipitated product can be washed with water and dried, for example under reduced pressure at about 40-60° C., to afford crystalline compound of formula (V').

Compound of Formula (V")

(V")

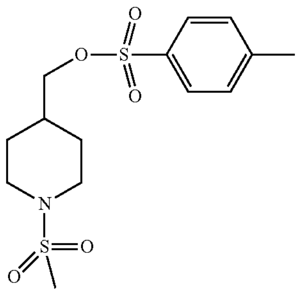

can be prepared using the method comprising the steps of a) reacting a compound of formula (IV)

(IV)

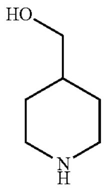

with chlorotrimethylsilane to obtain compound of formula (IVb)

(IVb)

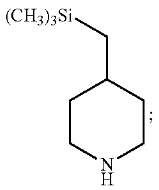

b) reacting the compound of formula (IVb) with methanesulfonyl chloride to obtain a compound of formula (IVc)

(IVc)

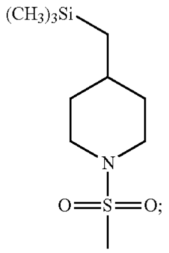

c) treating the compound of formula (IVc) with p-toluenesulfonic acid in the presence of methanol to obtain a compound of formula (IVd)

(IVd)

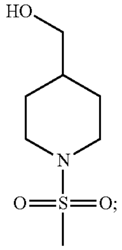

and d) reacting the compound of formula (IVd) with p-toluenesulfonyl chloride to obtain the compound of formula (V").

The method can be carried out by by adding to a reactor vessel under nitrogen atmosphere piperidin-4-ylmethanol, suitable solvent such as dichloromethane and a base such as 1,1,3,3-tetramethylguanidine. Chlorotrimethylsilane is then added gradually, for example during 1 h while keeping the temperature under 25° C. After stirring, for example for about 1 h, a base such as N-methylmorpholine is added followed by cooling the mixture, for example, to below 10° C. Methanesulfonyl chloride is then added slowly, for example during about 2 h, while keeping the temperature under 25° C. After the reaction is complete, the reaction can be quenched, for example, by adding 5% aqueous ammonia. The organic layer is isolated and combined with water followed by adjusting pH to 5-6, for example with citric acid. The organic layer is recovered and p-toluenesulfonic acid, for example in the form of monohydrate, is added together with methanol. Part of the solvent may be distilled off, acetonitrile is suitably added followed by further distillation of the solvent. The residue is allowed to cool and pyridine is added. The mixture is then added slowly, for example during about 1.5 h, to a mixture of pyridine and p-toluenesulfonyl chloride while keeping the temperature below 40° C. followed by stirring. Water is then added and the slurry is cooled, for example to about 0° C., during several hours, for example during about 3 h. The mixture can then be stirred for a period sufficient to complete precipitation, for example about 2 h, prior to isolation of the end product, for example by filtering. The precipitate can be washed with water and ice-cold isopropanol and dried, for example under reduced pressure at about 40-50° C., to afford compound of formula (V").

The invention is further illustrated by the following non-limiting examples.

Example 1. Preparation of 2-(Chloromethyl)-5-hydroxy-4H-pyran-4-one (II)

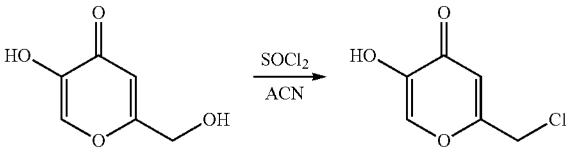

(I) (II)

To a reactor under nitrogen was added acetonitrile (525 ml) and kojic acid (I) (150 g). The mixture was heated to 45±5° C. Thionyl chloride (85 ml) was added over about 30 min while keeping temperature at 45±5° C. The mixture was agitated until completion of the reaction, for about 30 min. Water (300 ml) was added slowly over about 30 min while keeping temperature at 45±5° C. followed by mixing for about 1 h. The suspension was cooled to 5±5° C. over several hours followed by mixing for about 1 h. The product was collected and washed with water (450 ml) and acetonitrile (375 ml). The product was dried at 40-60° C. under vacuum to afford 143.7 g (84.8%) of the title compound as yellow crystalline powder.

Example 2. Preparation of 5-Hydroxy-2-(isoindolin-2-ylmethyl)-4H-pyran-4-one (III)

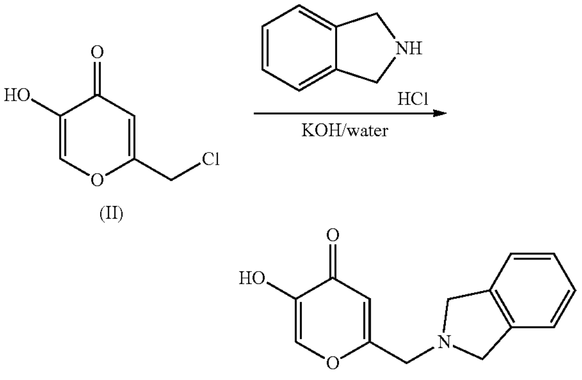

(II)

(III)

To a reactor under nitrogen was added water (510 ml) and isoindoline hydrochloride (145 g). Temperature of the mixture was adjusted to 5±5° C. Potassium hydroxide (48%, 44.0 ml) is added followed by 2-(chloromethyl)-5-hydroxy-4H-pyran-4-one (II) (120 g). More potassium hydroxide (48%, 161 ml) was added slowly while keeping temperature at 10±5° C. The mixture was held at this temperature until the reaction was complete (about 3 h). Another reactor under nitrogen was charged with acetone (600 ml) and acetic acid (77 ml) and heated to 35±5° C. The reaction mixture from the first reactor was transferred to the second reactor over about 30 min while keeping the temperature at 35±5° C. The resulting mass was stirred for about 30 min and then filtered. The product is washed with water (240 ml) and acetone (240 ml). The product was dried under vacuum at 40-60° C. to afford 159.7 g (87.8%) of the title compound as bright yellow crystalline powder.

Example 3. Preparation of 5-Hydroxy-2-(isoindolin-2-ylmethyl)-4H-pyran-4-one (III) (Alternative Method)

To a reactor under nitrogen was added dimethyl sulfoxide (300 ml), isoindo-line hydrochloride (72.7 g) and 2-(chloromethyl)-5-hydroxy-4H-pyran-4-one (II) (60.0 g). N,N-diisopropylethylamine (150 ml) was added and the mixture was heated to 50±5° C. The mixture was stirred until the reaction was complete (about 2-3 h) followed by adding acetonitrile (120 ml) and acetic acid (10.7 ml). Temperature was adjusted to 45±5° C. and water (240 ml) was added over about 30 min while keeping the temperature over 45° C. The mass was stirred for about 30 min and then cooled to 20±5° C. over 1 h. The product was collected and washed with water (180 ml) and acetonitrile (180 ml). The product was dried at 40-60° C. under vacuum to afford 81.9 g (90.1%) of the title compound as brown crystalline powder.

Example 4. Preparation of (1-(Methylsulfonyl)piperidin-4-yl)methyl methane sulfonate (V')

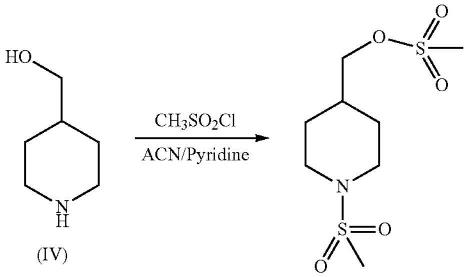

(IV) (V')

To a reactor under nitrogen was added acetonitrile (225 ml), pyridine (289 ml) and piperidin-4-ylmethanol (IV) (75 g). The temperature of the mixture was adjusted to 20±5° C. Methanesulfonyl chloride was slowly added over 30 min while keeping temperature below 35° C. The temperature was adjusted to 35±5° C. and the mixture was stirred for 2 h. Water (300 ml) was rapidly added followed by acetic acid (45 ml). The resulting mass was cooled over 3 h to 0±5° C. and mixed for 1 h prior to filtration. The product was washed with water (2 times 225 ml) and dried under vacuum at 40-60° C. to afford 153.3 g (86.8%) of the title compound as white crystalline powder.

Example 5. Preparation of (1-(Methylsulfonyl)piperidin-4-yl)methyl 4-methylbenzenesulfonate (V")

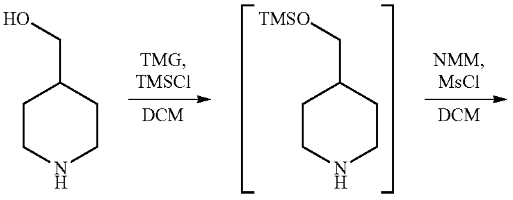

(IV)

-continued

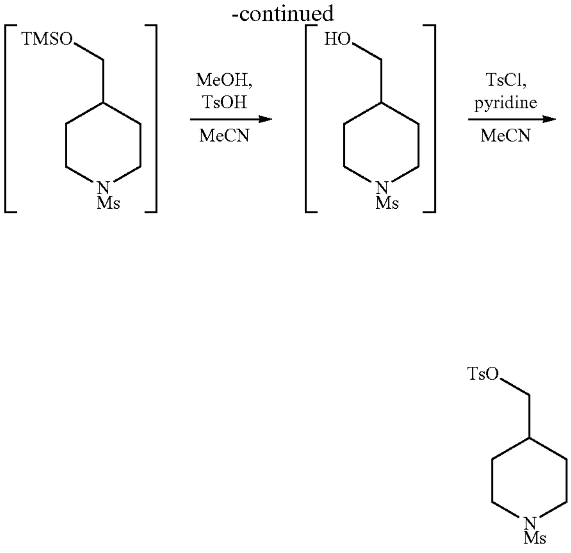

(V'')

To a reactor under nitrogen was added dichloromethane (700 ml), piperidin-4-ylmethanol (100 g) and 1,1,3,3-tetramethylguanidine (133 ml). The mixture was agitated until fully dissolved and then cooled to below 10° C. Chlorotrimethylsilane (138 ml) was added over about 1 h whilst keeping temperature below 25° C. followed by stirring for about 1 h at 20° C. N-Methylmorpholine (131 ml) was added and the mixture was cooled below 10° C. Methanesulfonyl chloride (82 ml) was added over about 2 h whilst keeping temperature below 25° C. The mixture was then stirred for about 30 min at 20° C. and then quenched with adding 5% aqueous ammonia (500 ml). After brief mixing the layers were separated. The organic layer was combined with water (400 ml) and the pH was adjusted to 5-6 with citric acid (about 35.0 g). The layers were separated and methanol (140 ml) and p-toluenesulfonic acid monohydrate (8.3 g) were added. About 500 ml was distilled off under atmospheric pressure. Acetonitrile (400 ml) was added and the distillation was continued until about 440 ml had been collected (end temperature about 84-85° C.). The residue was allowed to cool to 20° C. and pyridine (100 ml) was added. The solution was transferred to an addition funnel. To another vessel under nitrogen was added pyridine (320 ml) and p-toluenesulfonyl chloride (199 g) and the temperature was adjusted to 35° C. The contents of the addition funnel were added over about 1.5 h whilst keeping temperature below 40° C. followed by stirring for 2 h at 30° C. Water (600 ml) was added slowly. After about 150 ml had been added isopropanol (200 ml) was added to produce more stirrable mixture. The slurry was first heated to 40° C. and then cooled to 0° C. over several hours. The mass was allowed to stir for 2 h prior to filtration. The cake was washed with water (200 ml) and ice-cold isopropanol (200 ml). The product was dried under vacuum at 40-50° C. to give 226.5 g (75.1%) of the title compound.

Example 6. Preparation of 2-(Isoindolin-2-ylmethyl)-5-((1-(methylsulfonyl)-piperidin-4-yl)methoxy)-4H-pyran-4-one (1A)

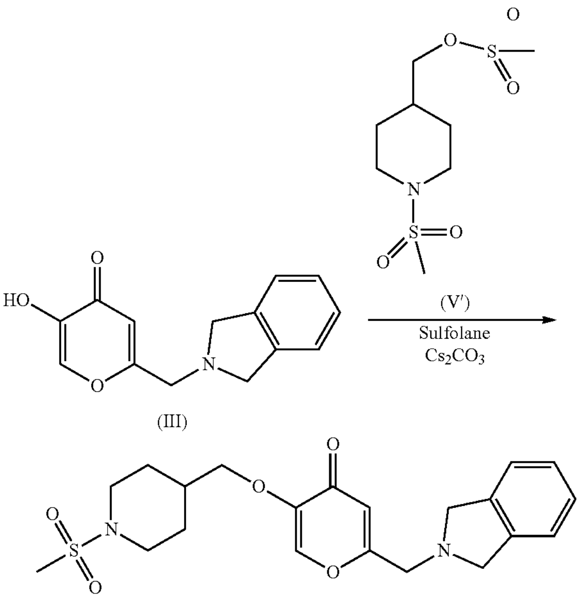

(III)

(1A)

To a vessel under nitrogen was added sulfolane (250 ml), 5-hydroxy-2-(iso-indolin-2-ylmethyl)-4H-pyran-4-one (III) (50 g), (1-(methylsulfonyl)piperidin-4-yl)methyl methane sulfonate (V') (64 g) and cesium carbonate (80 g). The mixture was heated to about 80° C. and stirred until the reaction was complete (about 3 h). The mixture was cooled to about 55° C. after which acetone (125 ml) was added followed by water (250 ml) whilst keeping temperature over 45° C. The temperature was adjusted to 50-55° C. and the mixture was seeded. Stirring was continued for about 30 min prior to cooling to 15±5° C. over about 3 h. The mass was stirred at least for 2 h prior to filtration. The product was washed with water (150 ml) and isopropanol (150 ml) and dried under vacuum at 40-60° C. to afford 66.9 g (77.8%) of the title compound as beige crystalline powder (in crystalline form 5).

Example 7. Preparation of 2-(Isoindolin-2-ylmethyl)-5-((1-(methylsulfonyl)-piperidin-4-yl)methoxy)-4H-pyran-4-one (1A) (Alternative Method)

To a reactor under nitrogen was added dimethyl sulfoxide (50 ml), 5-hydroxy-2-(isoindolin-2-ylmethyl)-4H-pyran-4-one (III) (10 g), (1-(methylsulfonyl)-piperidin-4-yl)methyl methane sulfonate (V') (12.8 g), TDA-1 (0.67 ml) and cesium carbonate (16.1 g). The mixture was heated to 65±5° C. and stirred until the reaction was complete (about 3 h). Isopropanol (33 ml) was added followed by water (55 ml) while keeping temperature over 60° C. The mixture was seeded and stirred for about 30 min. The mass was cooled to 15±5° C. over 3 h and stirred for at least 2 h prior to filtration. The product was washed with water (30 ml) and isopropanol (30 ml) and dried under vacuum at 40-60° C. to afford 15.0 g (87.1%) of the title compound as dark beige powder (in crystalline form 3).

Example 8. Preparation of 2-(Isoindolin-2-ylmethyl)-5-((1-(methylsulfonyl)-piperidin-4-yl)methoxy)-4H-pyran-4-one (1A) (Alternative Method)

To a reactor under nitrogen was added dimethyl formamide (500 ml), 5-hydroxy-2-(isoindolin-2-ylmethyl)-4H-pyran-4-one (III) (100 g), (1-(methylsulfonyl)piperidin-4-yl)methyl methane sulfonate (V') (128 g), cesium carbonate (161 g) and TDA-1 (6.6 ml). The mixture was heated to 70±3° C. and stirred until the reaction was complete (about 4 h). The mixture was cooled to 50±5° C. Isopropanol (250 ml) was added followed by water (500 ml) such that temperature was maintained at 50±5° C. The mixture was seeded and then cooled to 20±3° C. over about 3 h. Product was collected and washed with water (300 ml) and isopropanol (300 ml). Product was dried under vacuum at 40-60° C. to afford 142.4 g (82.8%) of the title compound as fine brown powder.

Example 9. Preparation of 2-(Isoindolin-2-ylmethyl)-5-((1-(methylsulfonyl)-piperidin-4-yl)methoxy)-4H-pyran-4-one (1A) (Alternative Method)

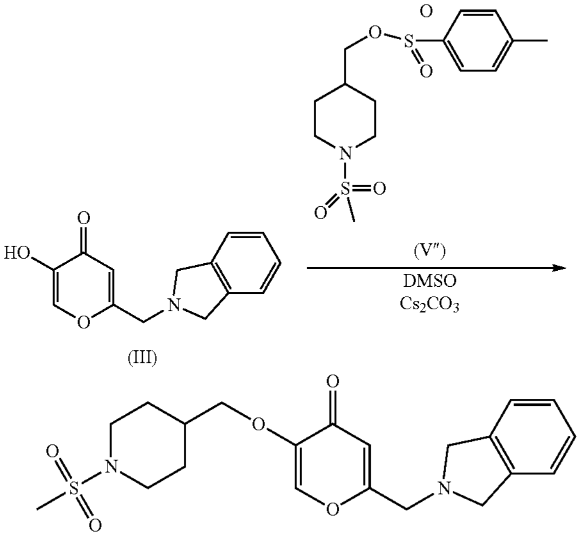

(III)

(1A)

To a reactor under nitrogen was added dimethyl sulfoxide (40 ml) 5-hydroxy-2-(isoindolin-2-ylmethyl)-4H-pyran-4-one (III) (8.0 g), (1-(methylsulfonyl)piperidin-4-yl)methyl 4-methylbenzenesulfonate (12.0 g) and cesium carbonate (12.3 g). The mixture was heated to about 55° C. and stirred for about 3 h. Isopropanol (24 ml) was added followed by dropwise addition of water (40 ml) over about 30 min whilst keeping temperature over 45° C. The mixture was seeded and then cooled to about 10° C. over about 2 h and stirred for 1 h. The product was collected by filtration and washed with 1:1 isopropanol:water (50 ml). The product was dried under vacuum at 40-60° C. to afford 10.4 g (75.6%) of the title compound.

The invention claimed is:

1. A process for the preparation of a compound of formula (1A) or a pharmaceutically acceptable salt thereof (1A)

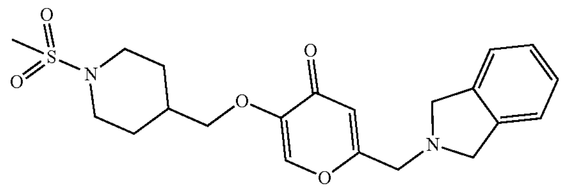

comprising the steps of either a) reacting a compound of formula (III)

(III)

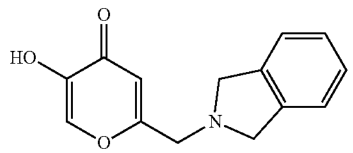

with a compound of formula (V)

(V)

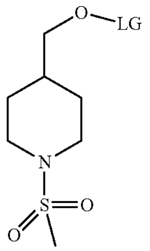

wherein LG is a leaving group selected from a mesyl or a tosyl group, in sulfolane in the presence of cesium carbonate;

b) adding acetone and water to the mixture; and c) isolating the compound of formula (1A), and optionally converting it to its pharmaceutically acceptable salt;

or a') reacting a compound of formula (III)

(III)

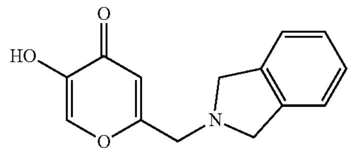

with a compound of formula (V)

(V)

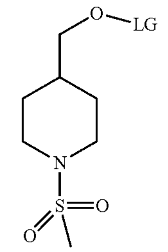

wherein LG is a leaving group selected from a mesyl or a tosyl group, in dimethyl sulfoxide or dimethyl formamide in the presence of cesium carbonate and tris[2-(2-methoxy-ethoxy)ethyl]amine);

b') adding isopropanol and water to the mixture; and c') isolating the compound of formula (1A), and optionally converting it to its pharmaceutically acceptable salt.

2. A process according to claim 1 comprising the steps of a) reacting a compound of formula (III)

(III)

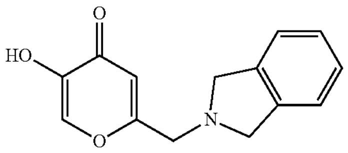

with a compound of formula (V)

(V)

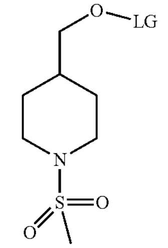

wherein LG is a leaving group selected from a mesyl or a tosyl group, in sulfolane in the presence of cesium carbonate;

b) adding acetone and water to the mixture; and c) isolating the compound of formula (1A), and optionally converting it to its pharmaceutically acceptable salt.

3. The process of claim 1, wherein the reaction temperature at step a) is from about 70 to about 90° C.

4. The process of claim 1, wherein step b) is carried out by adding acetone followed by water.

5. The process of claim 1, wherein the ratio acetone to water at step b) is from about 1:1 to about 1:3 per volume.

6. The process of claim 1, wherein the temperature after step b) is from about 45° C. to about 60° C.

7. The process of claim 1, wherein before step c) the mixture is cooled to a temperature form about 5° C. to about 25° C.

8. The process according to claim 1 comprising the steps of a') reacting a compound of formula (III)

(III)

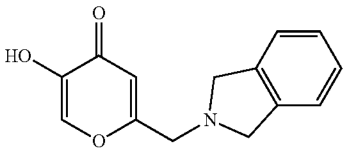

with a compound of formula (V)

(V)

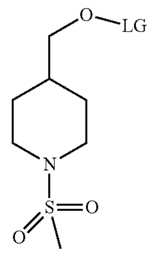

wherein LG is a leaving group selected from a mesyl or a tosyl group, in dimethyl sulfoxide or dimethyl formamide in the presence of cesium carbonate and tris[2-(2-methoxy-ethoxy)ethyl]amine);

b') adding isopropanol and water to the mixture; and c') isolating the compound of formula (1A), and optionally converting it to its pharmaceutically acceptable salt.

9. The process according to claim 8, wherein step a') is carried out in dimethyl sulfoxide.

10. The process according to claim 8, wherein the reaction temperature at step a') is from about 50° C. to about 70° C.

11. The process according to claim 8, wherein step b') is carried out by adding isopropanol followed by water.

12. The process according to claim 8, wherein the ratio of isopropanol to water at step b') is from about 1:1 to about 1:3 per volume.

13. The process according to claim 9, wherein before step c') the mixture is cooled to a temperature which is form about 5 to about 25° C.

14. The process according to claim 8, wherein step a') is carried out in dimethyl formamide.

15. The process according to claim 14, wherein the reaction temperature at step a') is from about 65° C. to about 75° C.

16. The process according to claim 14, wherein step b') is carried out by adding isopropanol followed by water.

17. The process according to claim 14, wherein the ratio of isopropanol to water at step b') is from about 1:1 to about 1:3 per volume.

18. The process according to claim 14, wherein the temperature after step b') is from about 40° C. to about 60° C.

19. The process according to claim 14, wherein before step c') the mixture is cooled to a temperature which is form about 10° C. to about 30° C.

20. A process for the preparation of a compound of formula (1A) or a pharmaceutically acceptable salt thereof (1A)

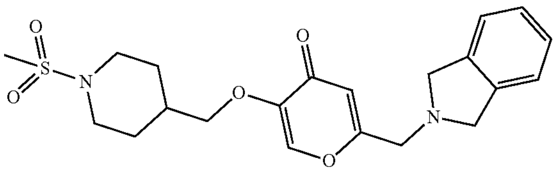

comprising the steps of either a) reacting a compound of formula (II)

(II)

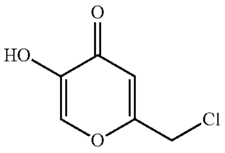

with isoindoline hydrochloride in water in the presence of potassium hydroxide;

b) transferring the reaction mixture of step a) into a mixture of acetone and acetic acid; and c) isolating the compound of formula (III);

or a') reacting a compound of formula (II)

(II)

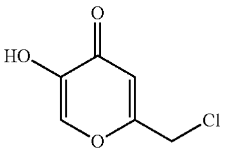

with isoindoline hydrochloride in dimethyl sulfoxide in the presence of N,N-diisopropylethylamine;

b') adding acetonitrile and water to the mixture; and c') isolating the compound of formula (III);

d) either reacting a compound of formula (III)

(III)

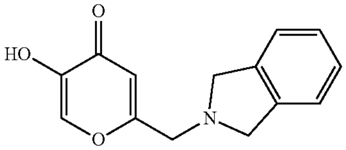

with a compound of formula (V)

(V)

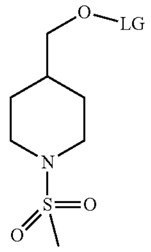

wherein LG is a leaving group selected from a mesyl or a tosyl group, in sulfolane in the presence of cesium carbonate;

e) adding acetone and water to the mixture; and f) isolating the compound of formula (1A), and optionally converting it to its pharmaceutically acceptable salt;

or d') reacting a compound of formula (III)

(III)

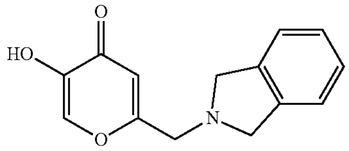

with a compound of formula (V)

(V)

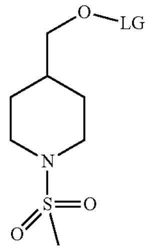

wherein LG is a leaving group selected from a mesyl or a tosyl group, in dimethyl sulfoxide or dimethyl formamide in the presence of cesium carbonate and tris[2-(2-methoxyethoxy)ethyl]amine);

e') adding isopropanol and water to the mixture; and f') isolating the compound of formula (1A), and optionally converting it to its pharmaceutically acceptable salt.

* * * * *